(12) United States Patent
Ochiai et al.

(10) Patent No.: US 10,352,950 B2
(45) Date of Patent: Jul. 16, 2019

(54) APPARATUS, METHOD, AND PROGRAM FOR COMPONENT MEASUREMENT

(71) Applicant: TERUMO KABUSHIKI KAISHA, Tokyo (JP)

(72) Inventors: Shouji Ochiai, Yamanashi (JP); Takeyuki Moriuchi, Yamanashi (JP); Masao Takinami, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 280 days.

(21) Appl. No.: 15/261,674

(22) Filed: Sep. 9, 2016

(65) Prior Publication Data

US 2016/0377634 A1 Dec. 29, 2016
US 2019/0049468 A9 Feb. 14, 2019

Related U.S. Application Data

(63) Continuation of application No. PCT/JP2015/054540, filed on Feb. 19, 2015.

(30) Foreign Application Priority Data

Mar. 14, 2014 (JP) .................. 2014-052206

(51) Int. Cl.
*G01N 33/48* (2006.01)
*G01N 33/72* (2006.01)
(Continued)

(52) U.S. Cl.
CPC ............. *G01N 33/721* (2013.01); *C12Q 1/54* (2013.01); *C12Y 101/03004* (2013.01); *C12Y 111/01* (2013.01); *G01N 21/27* (2013.01); *G01N 21/274* (2013.01); *G01N 21/31* (2013.01); *G01N 21/35* (2013.01); *G01N 21/78* (2013.01); *G01N 21/783* (2013.01); *G01N 33/66* (2013.01);
(Continued)

(58) Field of Classification Search
None
See application file for complete search history.

(56) References Cited

FOREIGN PATENT DOCUMENTS

EP 2261673 12/2010
JP H10-90062 4/1998
(Continued)

OTHER PUBLICATIONS

International Preliminary Report on Patentability for International Application No. PCT/JP2015/054540, dated Sep. 22, 2016.
(Continued)

*Primary Examiner* — Larry D Riggs, II
(74) *Attorney, Agent, or Firm* — Jason H. Vick; Sheridan Ross, PC

(57) ABSTRACT

Provided is a component measuring apparatus configured to determine a functional form that describes wavelength characteristics of a variation attributable to scattering (S ($\lambda$)). The apparatus then determines unknown one or more coefficients (p, q) based on a first relational expression that involves a variation attributable to absorption (H ($\lambda 1$)) and a group of second relational expressions that do not involve variations attributable to absorption (H ($\lambda 2a$), H ($\lambda 2b$), H ($\lambda 2c$)). The apparatus then corrects an absorbance measured at an arbitrary wavelength ($\lambda$) using a function where the one or more coefficients (p, q) are applied to the functional form so as to reduce or eliminate at least the effects of scattering of light.

20 Claims, 12 Drawing Sheets

(51) Int. Cl.
    *G01N 21/27*     (2006.01)
    *G01N 21/78*     (2006.01)
    *C12Q 1/54*     (2006.01)
    *G01N 21/31*     (2006.01)
    *G01N 21/35*     (2014.01)
    *G01N 33/66*     (2006.01)
    *G01N 21/84*     (2006.01)

(52) U.S. Cl.
    CPC ... *G01N 21/8483* (2013.01); *G01N 2201/061* (2013.01); *G01N 2201/12* (2013.01); *G01N 2333/805* (2013.01); *G01N 2333/904* (2013.01); *G01N 2333/908* (2013.01)

(56) References Cited

FOREIGN PATENT DOCUMENTS

| | | |
|---|---|---|
| JP | H11-241993 | 9/1999 |
| JP | 2011-017662 | 1/2011 |
| WO | WO 2005/027746 | 3/2005 |
| WO | WO 2009/037785 | 3/2009 |
| WO | WO 2009/123069 | 10/2009 |

OTHER PUBLICATIONS

International Search Report (with English machine translation) for International (PCT) Patent Application No. PCT/JP2015/054540, dated May 19, 2015, 5 pages.

Written Opinion (no translation) for International (PCT) Patent Application No. PCT/JP2015/054540, dated May 19, 2015, 3 pages.

APPARATUS, METHOD, AND PROGRAM FOR COMPONENT MEASUREMENT

CROSS REFERENCE TO RELATED APPLICATIONS

This Application is a continuation of and claims priority to PCT Application No. PCT/JP2015/054540, filed Feb. 19, 2015, which claim priority to Japanese Application Number 2014-052206, filed Mar. 14, 2014; both of these applications are incorporated herein by reference in their entirety for all that they teach and for all purposes.

TECHNICAL FIELD

The present invention relates to an apparatus, method, and program for component measurement for measuring an analyte in a bodily fluid based on the optical characteristics of a dye component contained in the bodily fluid before or after color reaction.

BACKGROUND

Absorptiometry is one of known techniques in biochemistry and medical fields for measuring a target component (also called, analyte) in a specimen bodily fluid. If the bodily fluid contains a large amount of a component other than the analyte, that component can cause such optical phenomena as absorption or scattering of light, resulting in acting as a disturbance agent in measurement. Thus, a variety of techniques for reducing the effects of such disturbance agent have been proposed in order to maintain accuracy in analyte measurement.

Japanese Patent Application, JP 11-241993 A, proposes a method for determining a scattering spectrum over an arbitrary wavelength region by applying a transmission spectrum obtained in measurement to a functional expression. The determined scattering spectrum is then subtracted at each wavelength, so that the transmission spectrum can be measured with improved accuracy.

SUMMARY

Technical Problem

Japanese Patent Application, JP 11-241993 A, describes the use of spectrophotometer for measuring the sample's transmission spectrum in paragraph [0009]. To obtain a number of data values that would be sufficient for establishing the graphs in FIGS. 2 and 3 in the document, however, use of a combination of a light source with spectral radiation characteristics of a wide range of wavelengths and a monochromator would be needed. Accordingly, apparatuses could be larger in size and costly to manufacture.

Solution to Problem

The embodiments herein address the above issue with an object of providing an apparatus, method, and program for component measurement, which can provide sufficiently accurate measurement of analytes even though the data size is small.

An embodiment of a component measuring apparatus measures an analyte in a bodily fluid based on optical characteristics of a dye component contained in the bodily fluid before or after color reaction, including: an absorbance acquisition section for acquiring a first observed value representing an absorbance at a specific wavelength in a first wavelength region in which a component other than the dye component has a relatively high light absorptivity and a group of second observed values representing absorbances at one or more wavelengths in a second wavelength region in which the light absorptivity is relatively low; a functional-form determination section for determining a functional form which describes wavelength characteristics of a variation attributable to scattering that indicates an absorbance variation attributable to scattering of light in the bodily fluid, and is specified by one or more coefficients; a coefficient calculation section for determining the unknown one or more coefficients based on a first relational expression for the first observed value, involving a variation attributable to absorption that indicates an absorbance variation attributable to absorption of light in the bodily fluid, and a group of second relational expressions for the second observed values, not involving the variation attributable to absorption; and an absorbance correction section for correcting an absorbance measured at an arbitrary wavelength using a function where the one or more coefficients determined by the coefficient calculation section are applied to the functional form determined by the functional-form determination section so as to reduce or eliminate at least the effects of the light scattering.

Thus, because the coefficient calculation section has been provided to calculate the unknowns (i.e., the one or more coefficients) based on: the single relational expression (first relational expression) which involves the variation attributable to absorption and which is for the first wavelength region in which the light absorptivity is relatively high; and relational expressions for the other values (second relational expressions) which do not involve the variation attributable to absorption and which are for the second wavelength region in which the light absorptivity is relatively low, the number of degrees of freedom for the variation attributable to absorption is minimum (i.e., one), which in turn means that a small number of data values suffices for approximating to the wavelength characteristics of the variation attributable to scattering with improved accuracy. Thus, the effects of light scattering can be appropriately reduced or eliminated even though the number of data values is small, whereby sufficient accuracy in analyte measurement can be provided.

Further, the absorbance correction section preferably corrects an absorbance measured at an arbitrary wavelength using the variation attributable to absorption so as to further reduce or eliminate the effects of the light absorption. The accuracy in analyte measurement is further improved by taking into account the effects of light absorption as well as light scattering.

Further, the coefficient calculation section preferably calculates the one or more coefficients based on the first relational expression expressing that the sum of an absorbance corresponding to concentration of the dye component, the variation attributable to scattering, and the variation attributable to absorption equals the first observed value, and the group of second relational expressions expressing that the sum of the absorbance corresponding to concentration and the variation attributable to scattering equals the second observed values.

Further, the coefficient calculation section preferably adds a constraint in calculating the one or more coefficients, which constraint being an absorption spectral similarity regardless of concentrations of the dye component. The incorporation of the absorption spectral similarity decreases the number of degrees of freedom for the absorbance corresponding to concentration, which means that a smaller number of data values will suffice.

Further, the functional-form determination section preferably determines the functional form that is specified by a number of the coefficients, which number being smaller than the number of the second observed values.

Further, the functional-form determination section preferably determines the functional form that is any one of polynomial function, power function, and exponential function. Because a scattering spectrum tends to attenuate monotonously and smoothly toward longer wavelengths, applying the scattering spectrum to one of the three forms of function will provide accurate approximation.

Further, the absorbance acquisition section preferably acquires the first observed value and the group of second observed values with wavelength intervals of at least 20 nm. By adopting wavelength intervals greater than predetermined ones, significant differences are attained for the variation attributable to scattering, and accordingly, the accuracy in approximating to the variation attributable to scattering is improved.

Further, the bodily fluid is preferably blood, the other component is preferably hemoglobin, and the absorbance acquisition section preferably acquires the first observed value in the first wavelength region of 400 nm to 600 nm and the group of second observed values in the second wavelength region of 600 nm to 1000 nm.

Further, the bodily fluid is preferably blood, and the dye component is preferably a component that develops color proportional to a glucose level in the blood.

An embodiment of a method measures an analyte in a bodily fluid based on optical characteristics of a dye component contained in the bodily fluid before or after color reaction, including: an acquiring step and an acquiring step of acquiring, respectively, a first observed value representing an absorbance at a specific wavelength in a first wavelength region in which a component other than the dye component has a relatively high light absorptivity, and a group of second observed values representing absorbances at one or more wavelengths in a second wavelength region in which the light absorptivity is relatively low; a determining step of determining a functional form which describes wavelength characteristics of a variation attributable to scattering that indicates an absorbance variation attributable to scattering of light in the bodily fluid, and is specified by one or more coefficients; a calculating step of determining the unknown one or more coefficients based on a first relational expression for the first observed value, involving a variation attributable to absorption that indicates an absorbance variation attributable to absorption of light in the bodily fluid, and a group of second relational expressions for the second observed values, not involving the variation attributable to absorption; and a correcting step of correcting an absorbance measured at an arbitrary wavelength using a function where the one or more coefficients are applied to the functional form so as to reduce or eliminate at least the effects of the light scattering.

An embodiment of a program for component measurement measures an analyte in a bodily fluid based on optical characteristics of a dye component contained in the bodily fluid before or after color reaction, including: an acquiring step and an acquiring step of acquiring, respectively, a first observed value representing an absorbance at a specific wavelength in a first wavelength region in which a component other than the dye component has a relatively high light absorptivity and a group of second observed values representing absorbances at one or more wavelengths in a second wavelength region in which the light absorptivity is relatively low; a determining step of determining a functional form which describes wavelength characteristics of a variation attributable to scattering that indicates an absorbance variation attributable to scattering of light in the bodily fluid, and is specified by one or more coefficients; a calculating step of determining the unknown one or more coefficients based on a first relational expression for the first observed value, involving a variation attributable to absorption that indicates an absorbance variation attributable to absorption of light in the bodily fluid, and a group of second relational expressions for the second observed values, not involving the variation attributable to absorption; and a correcting step of correcting an absorbance measured at an arbitrary wavelength using a function where the one or more coefficients are applied to the functional form so as to reduce or eliminate at least the effects of the light scattering.

Advantageous Effects

According to the novel apparatus, method, and program for component measurement, one or more coefficients, or the unknowns, are calculated based on: a single relational expression (a first relational expression) which involves a variation attributable to absorption and which is for a first wavelength region in which the light absorptivity is relatively high; and relational expressions for the other values (second relational expressions) which do not involve the variation attributable to absorption and which are for a second wavelength region in which the light absorptivity is relatively low, and therefore, the number of degrees of freedom for the variation attributable to absorption is minimum (i.e., one), which in turn means that a small number of data values suffices for approximating, to the wavelength characteristics, of a variation attributable to scattering with improved accuracy. Thus, the effects of light scattering can be appropriately reduced or eliminated even though the number of data values is small, whereby sufficient accuracy in analyte measurement can be provided.

DETAILED DESCRIPTION

Embodiments of the novel method for component measurement, in relation to the novel component-measuring apparatus and program for implementing the method, will now be described in detail with reference to the appended drawings.

Overall Configuration of Component Measuring Apparatus 10

Figure 1:
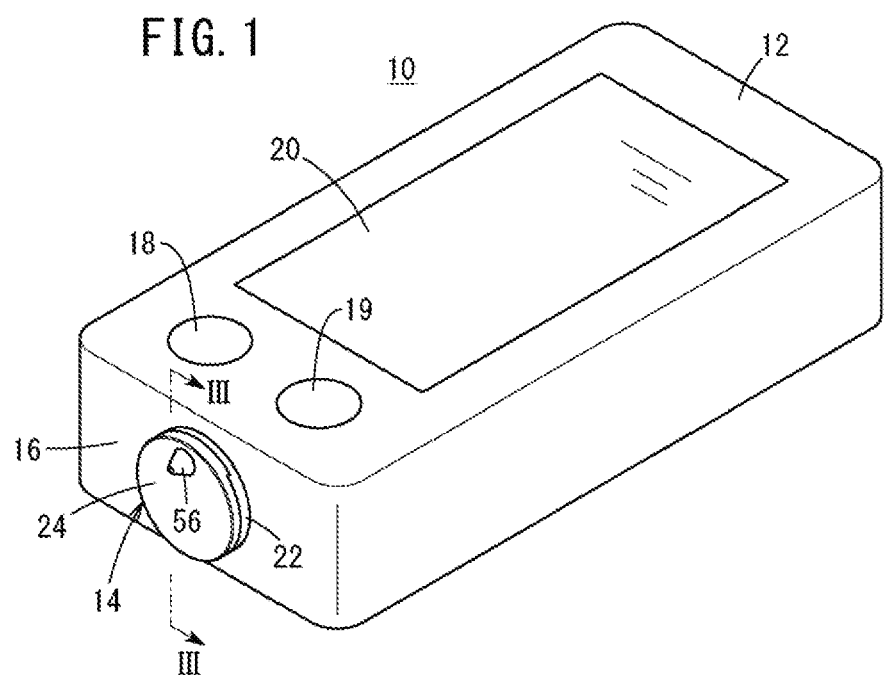
FIG. 1 is an orthogonal view of an embodiment of a component measuring apparatus.

FIG. 1 is an orthogonal view of an embodiment of a component measuring apparatus 10. The component measuring apparatus 10 may be a glucose meter configured to measure a specimen blood component (not shown).

The component measuring apparatus 10 can have a housing 12 made from, for example, a resin material, a tip attachment part 16 to which a test tip 14 is attached, buttons (more specifically, a power button 18 and an operation button 19) disposed on the top surface of the housing 12 near the tip attachment part 16, and a display monitor 20 disposed at the center of the top surface of the housing 12.

Although the housing 12, in the shown example, has a rectangular shape with rounded corners, the housing 12 is not limited to this shape. For example, the housing 12 may have such various shapes that users will find it easy to hold with one hand. The test tip 14 is attached to a forward end portion (i.e., the tip attachment part 16) of the component measuring apparatus 10 when the apparatus is used.

Configuration of Test Tip 14

Figure 2:
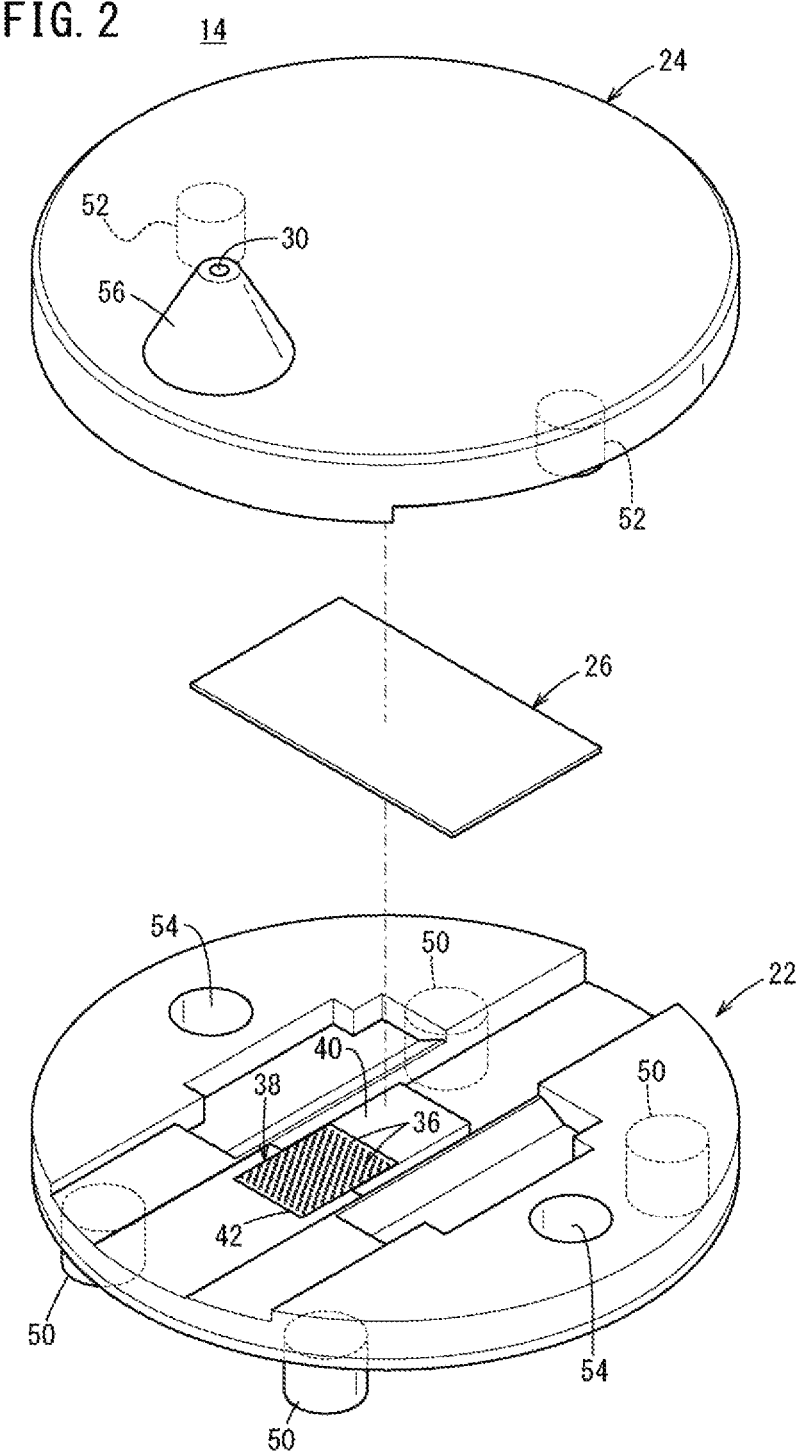
FIG. 2 is an exploded orthogonal view of an embodiment of a test tip as shown in FIG. 1.
Figure 3:
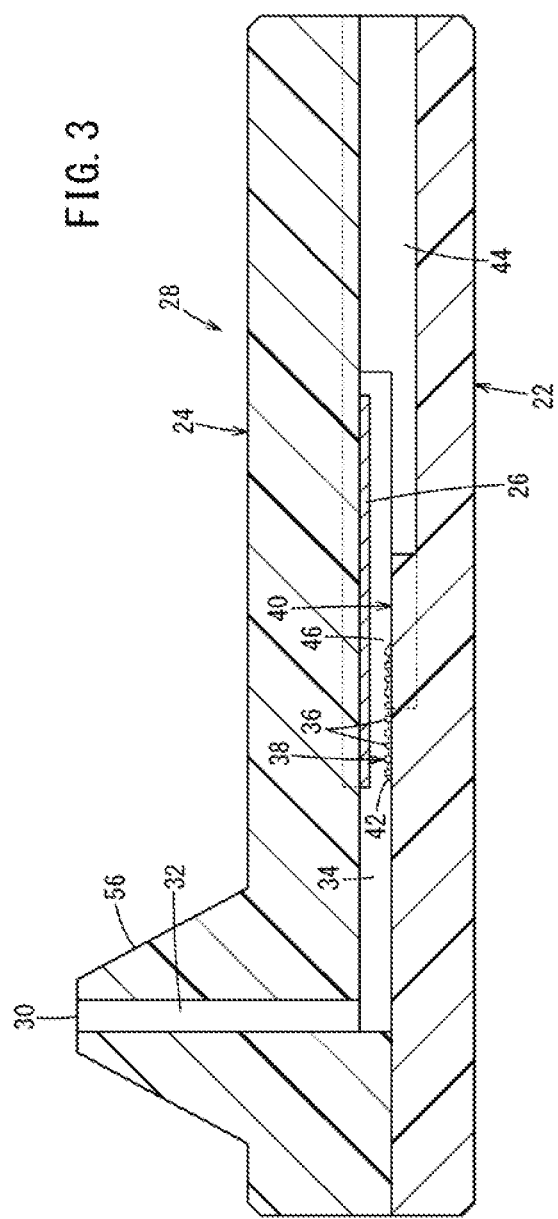
FIG. 3 is a cross-sectional view, taken along the line in FIG. 1, of an embodiment of a component measuring apparatus.

FIG. 2 is an exploded orthogonal view of the test tip 14 shown in FIG. 1. FIG. 3 is a cross-sectional view of the component measuring apparatus 10 taken along the III-III line in FIG. 1.

The test tip 14 may include a base member 22, a cover member 24 on top of the base member 22, and a gas permeable film 26 disposed between the base member 22 and the cover member 24. The base member 22 and the cover member 24 form a molded-product assembly 28 of the test tip 14.

As shown in FIG. 3, elements of the component measuring apparatus 10, formed in the molded-product assembly 28, can include: an entry port 30 through which blood can enter, an introduction channel 32 in communication with the entry port 30, a blood passageway 34 in communication with the introduction channel 32 and enabling passing of blood therethrough, a blood deployment section 38 having protrusions 36, and a measurement section 40 onto which light beams are directed for measurement. The measurement section 40 is disposed downstream of the blood deployment section 38. The blood deployment section 38 has been coated with a color reagent 42; the color reagent 42 will react with a blood component and produce color development proportional to the concentration of the component. A vent channel 44, through which air is communicated with the blood passageway 34, is also formed in the molded-product assembly 28.

By joining the base member 22 with the cover member 24, a space 46 of a predetermined size is formed inside the molded-product assembly 28 for reacting the color reagent 42 with blood. Although the space 46 may have any shape, its height is preferably in a range of, for example, 20 μm to 100 μm so that the sample blood can flow smoothly therethrough and that a wide range of blood levels can be measured, while keeping the necessary amount of sample blood low. The area of the space 46 is, for example, 0.2 mm$^2$ to 50 mm$^2$, preferably, so that optical measurement can be performed with only a small amount of blood.

As shown in FIG. 2, the base member 22 is a disk-like member in the shown example, provided with multiple (four, in this case) attachment protrusions 50 on its bottom surface for attachment and detachment of the base member 22 to and from the component measuring apparatus 10. The base member 22 can also have multiple (two, in the shown example) mating holes 54 for mating with mating protrusions 52 disposed on the bottom surface of the cover member 24.

As shown in FIGS. 1 to 3, a blood sampling nozzle 56 with a tapered tip is disposed on the cover member 24, protruded from a part near the periphery of the top surface of the cover member 24. The entry port 30 is formed at the tip of the blood sampling nozzle 56. Further, as shown in FIG. 3, the introduction channel 32 is disposed in the cover member 24 for communicating the entry port 30 with the blood passageway 34. Thus, when a drop of blood is applied to the tip of the blood sampling nozzle 56, the blood enters through the entry port 30 and is drawn through the introduction channel 32 into the blood passageway 34 by capillary action.

The component measuring apparatus 10 of a so-called colorimetric type irradiates the measurement section 40 with a beam of light, detects the amount of transmitted or reflected light, and obtains detected signals that correlate with color intensity that is proportional to a blood level. The component measuring apparatus 10 then refers to a calibration curve that has been established in advance to measure an analyte, for example, quantify the concentration of the analyte.

Electrical Block Diagram of Component Measuring Apparatus 10

Figure 4:
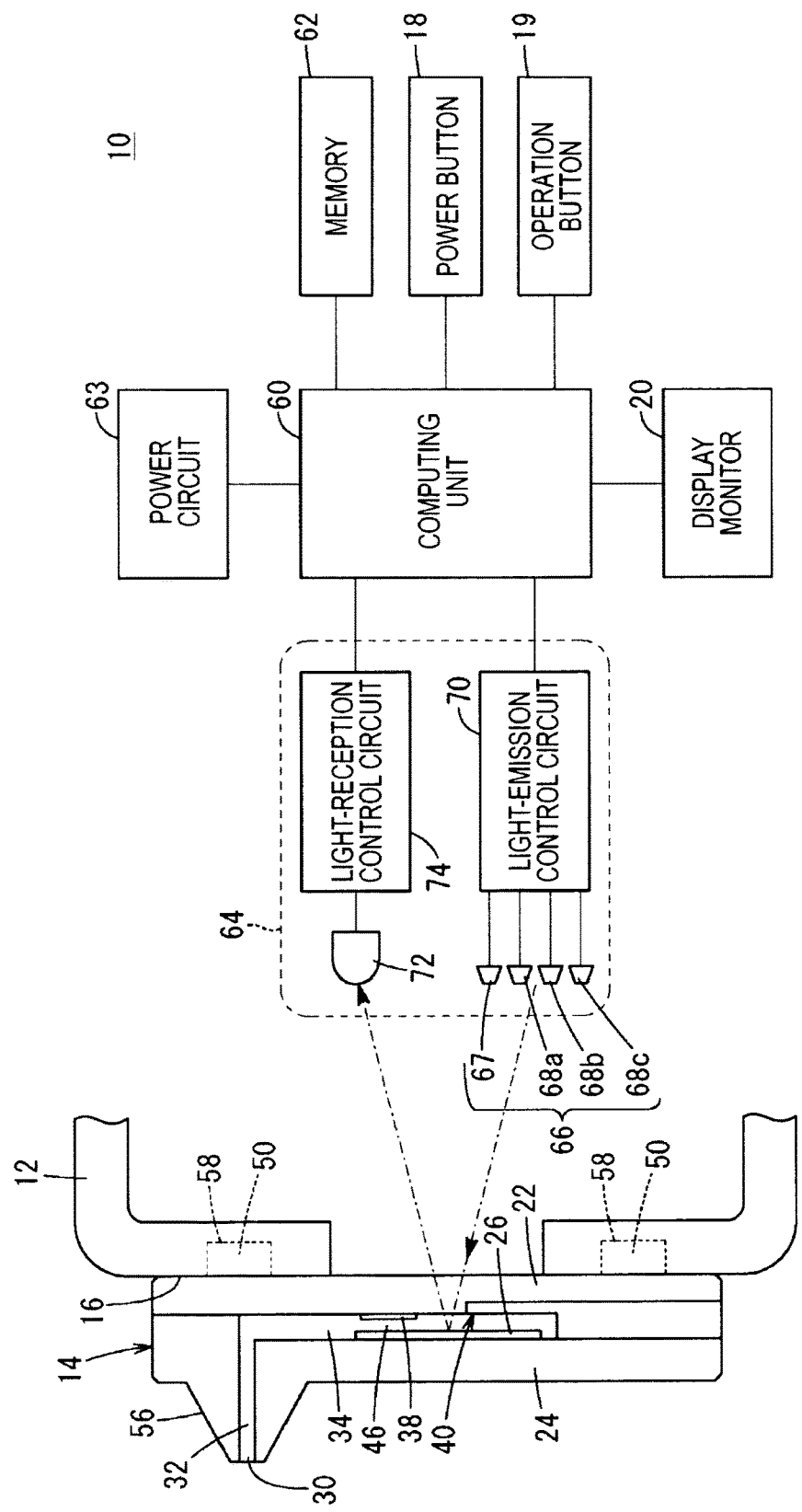
FIG. 4 is an electrical block diagram of an embodiment of the component measuring apparatus shown in FIG. 1.

FIG. 4 is an electrical block diagram of the component measuring apparatus 10 shown in FIG. 1. To the left, a partially enlarged cross-sectional view of the forward end portion of the component measuring apparatus 10, including the test tip 14, is shown. Attachment holes 58 that can mate with the attachment protrusions 50 are provided in the tip attachment part 16; the test tip 14 is attached to the component measuring apparatus 10 by the mating of the attachment protrusions 50 and the attachment holes 58.

The component measuring apparatus 10 further has a computing unit 60, a memory 62, a power circuit 63, and an optical measurement system 64 as well as the power button 18, the operation button 19, and the display monitor 20 mentioned above.

The computing unit 60 includes a micro-processing unit (MPU) or a central processing unit (CPU) and can perform control operations for various parts of the apparatus by reading and executing programs stored in the memory 62 or other medium. The memory 62 is a volatile or non-volatile, non-transitory storage medium and allows various data (including programs), which are necessary for performing component measurement by the present method, to be read out or written in. The power circuit 63 supplies or shuts off power to the computing unit 60 and other parts of the component measuring apparatus 10 in response to the operation of the power button 18.

The optical measurement system 64 is an optical system that can acquire optical characteristics of a dye component included in blood after color development. Specifically, the optical measurement system 64 includes a light emitter 66 (including four kinds of light sources 67, 68a, 68b, and 68c, in the shown example), a light-emission control circuit 70, a light receiver 72 (a single light-receiving device in the shown example), and a light-reception control circuit 74.

The light sources 67, 68a, 68b, and 68c emit light beams of different spectral radiation characteristics, for example, beams of visible light and infrared light. The peak wavelengths of the light sources 67, 68a, 68b, and 68c are λ1, λ2a, λ2b, and λ2c, respectively. The different kinds of light sources 67, 68a, 68b, and 68c usable in the apparatus can include light-emitting diode (LED) devices, organic electroluminescence (EL) devices, inorganic EL devices, laser diode (LD) devices, and other light-emitting devices.

The light receiver 72 receives light reflected from the test tip 14, more specifically, from the cover member 24. A photodiode (PD) device, a photo conductor (photoconductive device), a photo transistor (PT), or other photoelectric conversion device can be used for the light receiver 72.

The light-emission control circuit 70 supplies or shuts off electric driving signals to the light sources 67, 68a, 68b, and 68c to switch on or off these light sources. The light-reception control circuit 74 performs logarithm conversions and A/D conversions on analogue signals from the light receiver 72 to yield digital signals, which are hereinafter called "detected signals."

Functional Block Diagram of Computing Unit 60

Figure 5:
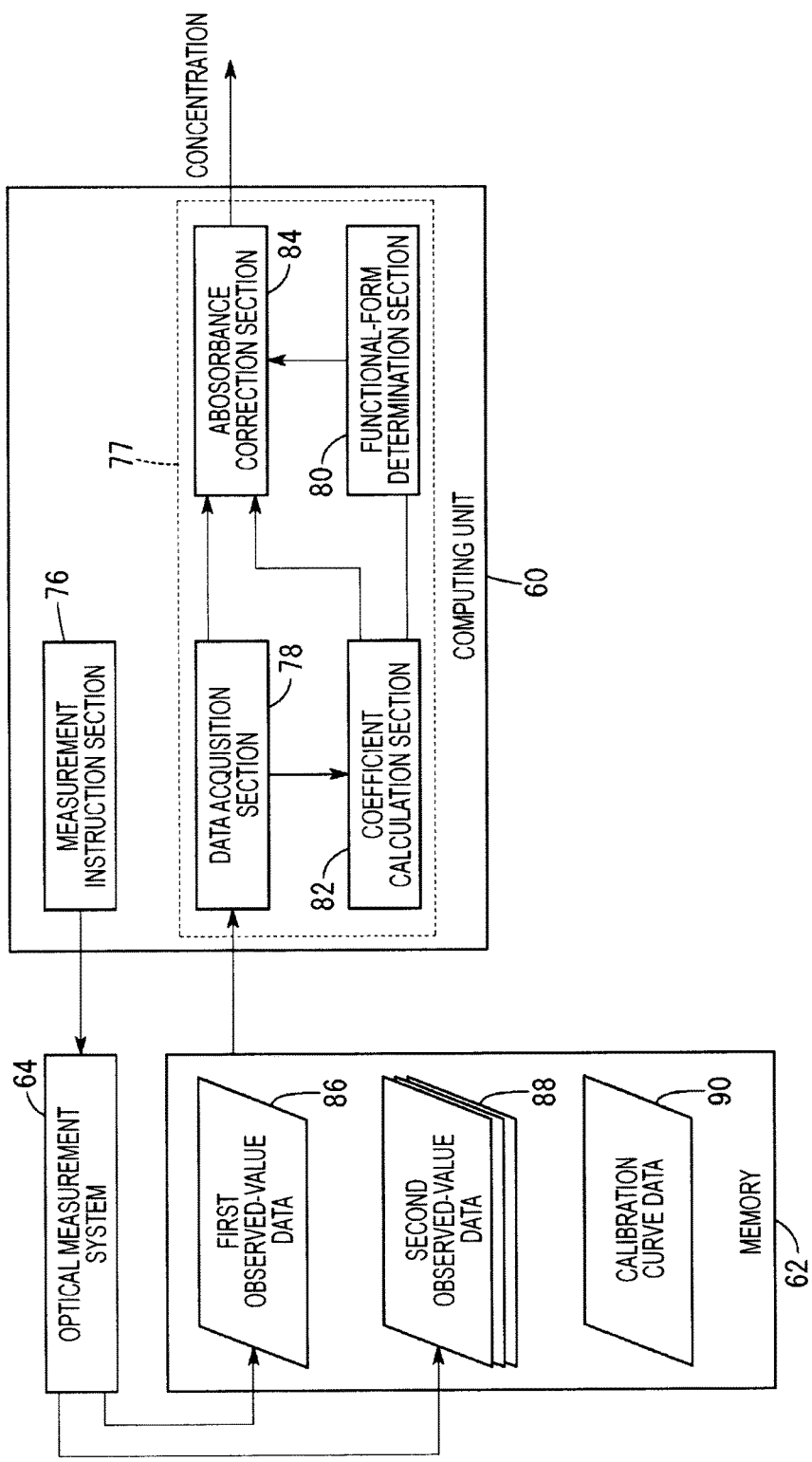
FIG. 5 is a functional block diagram for an embodiment of a computing unit shown in FIG. 4.

FIG. 5 is a functional block diagram for the computing unit 60 shown in FIG. 4. The computing unit 60 has a measurement instruction section 76 and a concentration quantifying section 77 perform their functions, that is, the measurement instruction section 76 instructs the optical measurement system 64 to perform measurement, and the concentration quantifying section 77 quantifies the concentration of a dye component using various kinds of data.

The concentration quantifying section 77 has a data acquisition section 78 (absorbance acquisition section) for acquiring various kinds of data needed in quantifying processes, a functional-form determination section 80 for determining a form of function (herein used interchangeably with "functional form") for a variation attributable to scattering S (λ) to be described later, a coefficient calculation section 82 for calculating one or more coefficients (for example, two coefficients p and q) for specifying the determined functional form, and an absorbance correction section 84 for estimating an absorbance after reducing or eliminating the effects of light scattering, that is, an absorbance corresponding to concentration D (λ).

In the shown example, the memory 62 stores first observed-value data 86 correlated with observed absorbance A (λ1), a group of second observed-value data 88 correlated with observed absorbances A (λ2a), A (λ2b), and A (λ2c), and calibration curve data 90 for describing relationships between absorbance and physical quantities, for example, hematocrit levels or concentrations.

Issues Concerning Measurement

The component measuring apparatus 10 according to the embodiment is configured as described above. Before describing the operation of the component measuring apparatus 10, some issues concerning blood component measurement using whole blood will be described. The term "whole blood" as used herein refers to blood containing all components (i.e., plasma, red blood cells, white blood cells, platelets, etc.), none of which having been separated.

In the following, an erioglaucine-added whole blood analysis will be described in detail by way of example, provided that a dye component is produced by reaction of a certain component (for example, glucose) contained in whole blood and the color reagent 42.

Figure 6A:
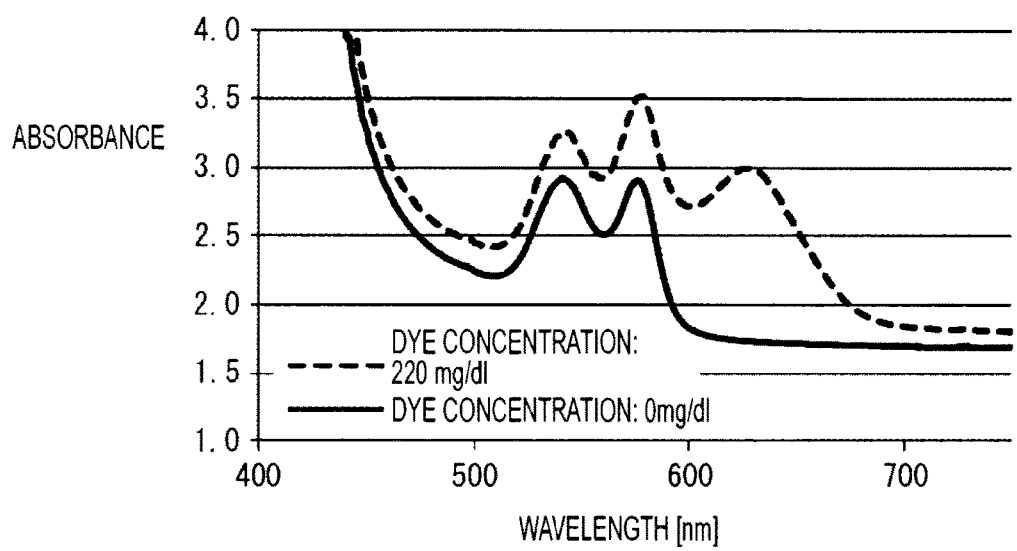
FIG. 6A is a graph presenting absorption spectra of whole blood.
Figure 6B:
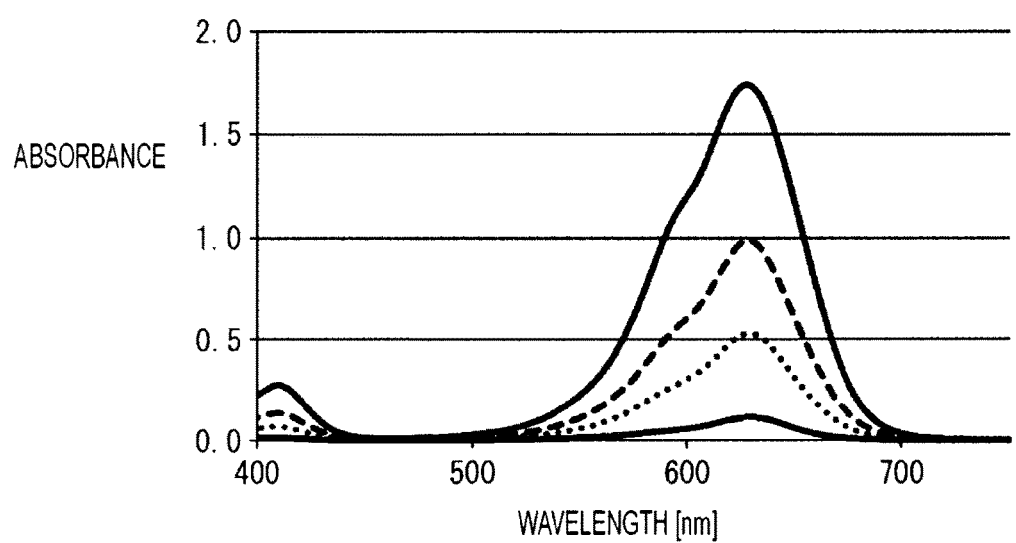
FIG. 6B is a graph presenting absorption spectra of erioglaucine.

FIG. 6A is a graph presenting absorption spectra of whole blood; FIG. 6B is a graph presenting absorption spectra of erioglaucine. In the graphs, absorbance (unitless) is on the vertical axis versus wavelength λ (unit: nm) on the horizontal axis.

The solid line shown in FIG. 6A presents an absorption spectrum of whole blood where the erioglaucine concentration (also called "dye concentration") is 0 mg/dL. The spectrum is a trend curve in which the absorbance is attenuated toward longer wavelengths, with two peaks at about λ=540 nm and λ=585 nm. These two peaks are attributable to the absorption characteristics of hemoglobin contained in red blood cells.

The broken line shown in the graph presents an absorption spectrum of whole blood with a dye concentration of 220 mg/dL. Compared with the solid line spectrum, the broken line spectrum shows higher absorbance over a wavelength range of visible light with a distinct peak at about λ=630 nm. It follows that this peak is attributable to the absorption characteristics of erioglaucine.

FIG. 6B is a graph presenting absorption spectra of whole blood with different dye concentrations. As can be seen from this figure, the absorption spectra are similar to each other regardless of dye concentrations.

In general, results of measurement of an analyte or a dye component, more specifically erioglaucine, can be affected by some optical phenomena caused by other component(s), if any, contained in the same sample. For example, (1) "scattering of light" by blood components (in particular, blood cells) and (2) "absorption of light" by components (in particular, hemoglobin) other than the dye component, can lead to reading of an absorbance value that is greater than the true value.

The above-mentioned optical phenomena can be described by a mathematic model that is represented by the following expression (1):

$$A(\lambda) = D(\lambda) + S(\lambda) + H(\lambda) \tag{1}$$

In the expression above, A (λ) is the absorbance observed in the actual measurement (i.e., unprocessed data), and can be called "observed absorbance" hereinafter; S (λ) is the absorbance variation attributable to scattering of light in blood, and can be called "variation attributable to scattering" hereinafter; D (λ) is the absorbance that corresponds to the concentration of a dye component, and can be called "absorbance corresponding to concentration" hereinafter; and H (λ) is the absorbance variation attributable to absorption of light by other component(s), and can be called "variation attributable to absorption" hereinafter.

The expression (1) can be modified as is shown in the following expression (2) to provide the absorbance corresponding to concentration D (λ):

$$D(\lambda) = A(\lambda) - S(\lambda) - H(\lambda) \tag{2}$$

To estimate the unknown variation attributable to scattering S (λ) and variation attributable to absorption H (λ), however, the observed absorbance A (λ) needs to be obtained at different wavelengths (λ), and a plurality of expressions (1) need to be established as a system. For example, in order to obtain multiple values of the observed absorbance A (λ), a light source with spectral radiation characteristics of a wide range of wavelengths and a monochromator must be used in combination. Consequently, the component measuring apparatus 10 would be large in size and costly to manufacture.

Further, pretreating samples may be an option for the fundamental solution for the issues mentioned above. "Pretreatment" includes various treatments for reducing or eliminating unnecessary components from the sample before conducting measurement, which treatments can include, by way of example, sample centrifugation and addition of surfactant. Unfortunately, however, such pretreatments can alter the dye component and change its properties or concentrations. Moreover, extra equipment and time are needed for pretreatments, which is burdensome in terms of investment and labor.

Hence, proposed is a method for analyte measurement that is sufficiently accurate even though the number of data values is relatively small, without using the above-mentioned pretreatments or apparatus configuration.

Operation of Component Measuring Apparatus 10

Figure 7:
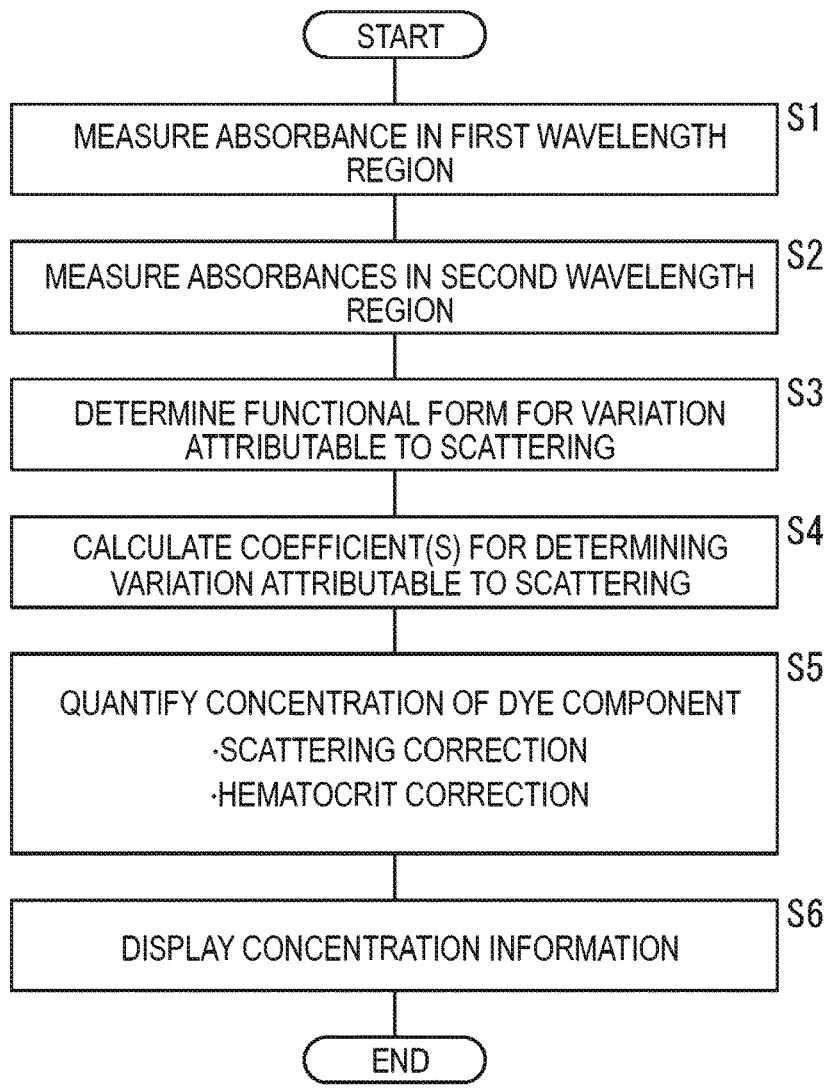
FIG. 7 is a flow chart illustrating operation of an embodiment of the component measuring apparatus shown in FIGS. 1 to 4.

The operation of the component measuring apparatus 10 will now be described with reference to, mainly, the functional block diagram in FIG. 5 and the flow chart in FIG. 7.

In step S1, the optical measurement system 64 measures absorbance at a specific wavelength (wavelength $\lambda 1$) in a first wavelength region R1, which absorbance will be called "first observed value" hereinafter. The first wavelength region R1 herein means a wavelength region in which a component other than the dye component, in particular hemoglobin, has a relatively high light absorptivity.

Figure 8:
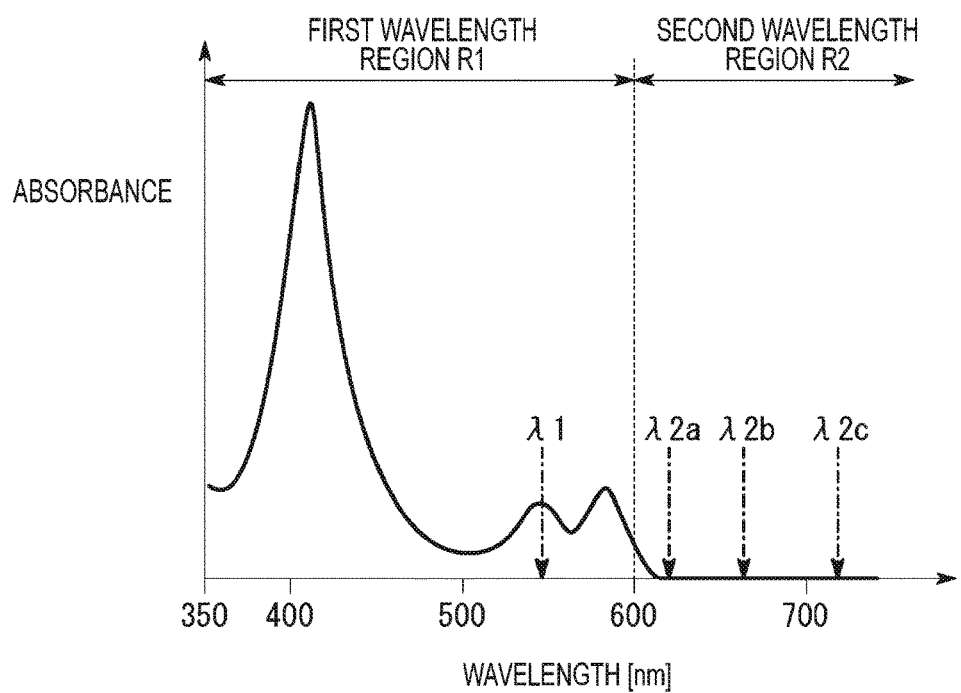
FIG. 8 is a schematic view illustrating a first wavelength region and a second wavelength region.

FIG. 8 is a schematic view illustrating the first wavelength region R1 and a second wavelength region R2. In the graph, absorbance is on the vertical axis versus wavelength on the horizontal axis. The graph presents an absorption spectrum of oxyhemoglobin.

As can be seen from FIG. 8, the absorption spectrum has three peaks at about $\lambda$=420 nm, 540 nm, and 585 nm, and is extremely attenuated in the wavelength region where $\lambda$>600 nm. When the first wavelength region R1 and the second wavelength region R2 are separated by a boundary of 600 nm, the shorter wavelength side from the boundary is the first wavelength region R1 and the longer wavelength side from the boundary is the second wavelength region R2, the absorptivity being relatively higher in the first wavelength region R1 than the second wavelength region R2.

By way of example, the light source 67 is an LED device whose spectral radiation characteristics include a sharp peak at about $\lambda 1$=540 nm. Note that this $\lambda 1$ coincides with one of the peak wavelengths of the hemoglobin absorption spectrum (see FIG. 8).

To begin measurement, the measurement instruction section 76 instructs the optical measurement system 64, more specifically, the light-emission control circuit 70, to start a first run of measurement. Receiving this instruction, the optical measurement system 64 directs a beam of light from the light source 67 to the test tip 14 and in turn detects the amount of reflected light. In this way the optical measurement system 64 obtains a detected signal correlated with an observed absorbance A ($\lambda 1$).

The computing unit 60 has the memory 62 temporarily store the detected signal in the form of first observed-value data 86. The data acquisition section 78 then acquires the first observed-value data 86 by reading from the memory 62 with the first observed-value data 86 being linked to the specific wavelength ($\lambda 1$).

In step S2, the optical measurement system 64 measures absorbance at one or more wavelengths in the second wavelength region R2 to determine what is hereinafter called "a group of second observed values." Note that, the second wavelength region R2 refers to a region of wavelengths in which the other component or hemoglobin has a relatively low absorptivity.

By way of example, the light sources 68a, 68b, and 68c are all LED devices whose spectral radiation characteristics include sharp peaks at about $\lambda 2a$=610 nm, $\lambda 2b$=630 nm, and $\lambda 2c$=650 nm, respectively. Note that this $\lambda 2b$ coincides with the peak wavelengths of the erioglaucine absorption spectra (see FIG. 6B).

The measurement instruction section 76 sequentially switches on and off the light sources 68a, 68b, and 68c to obtain detected signals correlated with the observed absorbance A ($\lambda 2a$), A ($\lambda 2b$), and A ($\lambda 2c$), respectively. The computing unit 60 has the memory 62 temporarily store these detected signals in the form of second observed-value data 88. The data acquisition section 78 then acquires the second observed-value data 88 by reading from the memory 62 with the second observed-value data 88 being linked to the wavelengths $\lambda 2a$, $\lambda 2b$, and $\lambda 2c$.

It should be noted that the first wavelength region R1 and the second wavelength region R2 are appropriately set depending on the kind of bodily fluid and analyte. For example, in the case of blood hemoglobin, the data acquisition section 78 will acquire first observed-value data 86 obtained in a first wavelength region R1 of 400 nm to 600 nm and second observed-value data 88 obtained in a second wavelength region R2 of 600 nm to 1000 nm.

Further, it is preferable that the data acquisition section 78 acquires the first observed-value data 86 and the second observed-value data 88 in which data values have been observed at wavelength intervals of at least 20 nm. By adopting wavelength intervals greater than predetermined ones, significant differences are attained for the variation attributable to scattering S ($\lambda$), and accordingly the accuracy in approximating to the variation attributable to scattering S ($\lambda$) is improved.

In step S3, the functional-form determination section 80 determines a form of function for the variation attributable to scattering S ($\lambda$), which form of function is specified by at least one coefficient. More specifically, the functional-form determination section 80 determines a form of function specified by a certain number of coefficients, which number is smaller than the number of the second observed values. In this way, the coefficients will not be indefinite numbers in association with the relational expressions and degrees of freedom to be described later.

The functional-form determination section 80 may employ any form of function, but it preferably employs any one of polynomial function, power function, and exponential function. Because a scattering spectrum tends to attenuate monotonously and smoothly toward longer wavelengths, applying the scattering spectrum to one of the three forms of function will provide accuracy in approximation.

In embodiments, a form of function that is specified by two coefficients p and q is used. For example, for a polynomial function, power function, or exponential function, the functional form is expressed by the following expressions (3) to (5), respectively:

$$S(\lambda)=p\cdot\lambda+q \tag{3}$$

$$S(\lambda)=p\cdot\lambda^q \tag{4}$$

$$S(\lambda)=p\cdot\exp(q\cdot\lambda) \tag{5}$$

Alternatively, the functional-form determination section 80 may determine a fixed functional form or a functional form (and the number of coefficients) that varies depending on the measurement conditions. Such measurement conditions can include, byway of example without limitation, the kind of bodily fluid, analyte, and test tip 14.

In step S4, the coefficient calculation section 82 uses the observed absorbances A's ($\lambda$) obtained in steps S1 and S2 to calculate one or more coefficients that specify the functional form determined in step S3. The coefficient calculation section 82 establishes a system of two kinds of relational expressions depending on the properties of wavelengths to determine an adequate coefficient(s). For the purpose of illustration and by way of example, the coefficient(s) is determined by the functional form as expressed in the expression (3) which is a linear function of $\lambda$.

A relational expression for the first wavelength region R1 (hereinafter called "first relational expression") is an expression expressing that the sum of the absorbance corresponding to concentration D ($\lambda$), the variation attributable to scattering S ($\lambda$), and the variation attributable to absorption H ($\lambda$) equals the observed absorbance A ($\lambda$). Specifically, this is expressed in the expression (6):

$$A(\lambda 1) = D(\lambda 1) + (p \cdot \lambda 1 + q) + H(\lambda 1) \tag{6}$$

Further, a relational expression for the second wavelength region R2 (hereinafter called "second relational expression") is an expression expressing that the sum of the absorbance corresponding to concentration D ($\lambda$) and the variation attributable to scattering S ($\lambda$) equals the observed absorbance A ($\lambda$). Specifically, this is expressed in the expressions (7) to (9):

$$A(\lambda 2a) = D(\lambda 2a) + (p \cdot \lambda 2a + q) \tag{7}$$

$$A(\lambda 2b) = D(\lambda 2b) + (p \cdot \lambda 2b + q) \tag{8}$$

$$A(\lambda 2c) = D(\lambda 2c) + (p \cdot \lambda 2c + q) \tag{9}$$

Further, absorption spectral similarity, such as that shown in FIG. 6B, is noted. Specifically, between two arbitrary wavelengths, the ratio of dye component absorbance is hypothesized to be constant regardless of the concentrations. For this the following expressions (10) to (13) are established:

$$C1 = D(\lambda 1)/D(\lambda 2b) \tag{10}$$

$$C2a = D(\lambda 2a)/D(\lambda 2b) \tag{11}$$

$$C2b = D(\lambda 2b)/D(\lambda 2b) = 1 \tag{12}$$

$$C2c = D(\lambda 2c)/D(\lambda 2b) \tag{13}$$

In the expressions above, C1, C2a, C2b and C2c are known values that have been experimentally obtained in advance. The reason for "C2b=1" is that the absorbance corresponding to concentration D ($\lambda 2b$) is to be determined ultimately. According to the example shown in FIG. 6B, C1=0.0854, C2a=0.7968, and C2c=0.6479.

Hence, the coefficient calculation section 82 may add a constraint, which is the absorption spectral similarity regardless of the concentrations of the dye component. The incorporation of the absorption spectral similarity decreases the number of degrees of freedom for the absorbance corresponding to concentration D ($\lambda$), which means that a smaller number of data values will suffice.

By substituting the expressions (10) to (13) into the expressions (6) to (9), a system of linear equations concerning the four unknowns p, q, D ($\lambda 2b$), and H ($\lambda 1$) is derived as the following expressions (14) to (17):

$$A(\lambda 1) = C1 \cdot D(\lambda 2b) + (p \cdot \lambda 1 + q) + H(\lambda 1) \tag{14}$$

$$A(\lambda 2a) = C2a \cdot D(\lambda 2b) + (p \cdot \lambda 2a + q) \tag{15}$$

$$A(\lambda 2b) = C2b \cdot D(\lambda 2b) + (p \cdot \lambda 2b + q) \tag{16}$$

$$A(\lambda 2c) = C2c \cdot D(\lambda 2b) + (p \cdot \lambda 2c + q) \tag{17}$$

Because the number of the relational expressions and the number of the unknowns (degrees of freedom) are equal, the values for p, q, D ($\lambda 2b$), and H ($\lambda 1$) are uniquely determined by solving the system of linear equations. Incidentally, if the functional form for the variation attributable to scattering S ($\lambda$) is either the expression (4) or the expression (5), the same calculation procedures as mentioned above can be taken; only it involves solving a system of non-linear equations because the relational expression involves a non-linear function.

Figure 9:
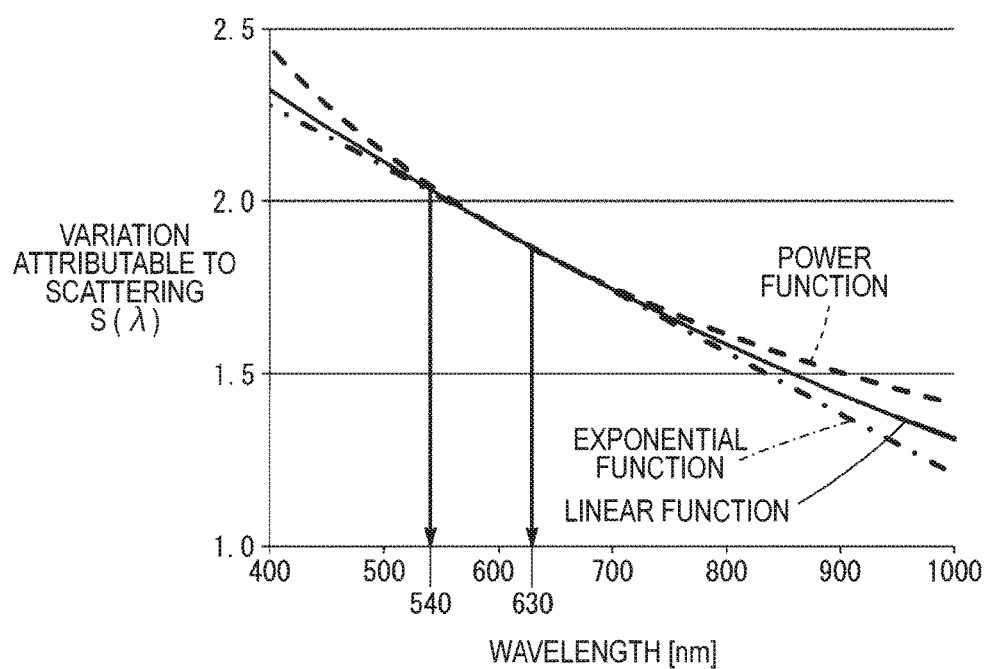
FIG. 9 is a graph presenting the results of calculation of variation attributable to scattering.

FIG. 9 is a graph presenting the results of calculation of the variation attributable to scattering S ($\lambda$). In the graph, the variation attributable to scattering S ($\lambda$) is on the vertical axis versus wavelength ($\lambda$) on the horizontal axis. The solid line presents the result of calculation by a "linear function;" the broken line presents the result of calculation by a "power function;" and the phantom line presents the result of calculation by an "exponential function."

In the graph, the coefficients p and q have been determined so that two points, specifically, $\lambda 1$=540 nm and $\lambda 2b$=630 nm, are commonly passed through. As can be seen from the graph, there is little difference by functional form within a wavelength region in which $\lambda 1$ is shorter than $\lambda$ which is shorter than $\lambda 2a$. Shifted away from this wavelength region, however, the calculation results start to show significant differences among the selected functional forms. Thus, it is desirable that a functional form is selected so as to best approximate to the actual variation attributable to scattering S ($\lambda$).

In step S5, the concentration quantifying section 77 quantifies the concentration of the analyte erioglaucine using p, q, D ($\lambda 2b$), and H ($\lambda 1$) calculated in step S4. Prior to the quantification process, the absorbance correction section 84 reduces or eliminates the effects of light scattering and/or absorption in the blood by correcting the absorbance corresponding to concentration D ($\lambda 2b$).

First, a hematocrit level Hct (unit: %) at the specific wavelength $\lambda 1$ is calculated. The "hematocrit level" indicates the ratio of red blood cells in blood by volume. The hematocrit level Hct is calculated by the following expression (18), using a calibration curve f ($\bullet$) at the specific wavelength $\lambda 1$:

$$Hct = f(H(\lambda 1)) \tag{18}$$

Here, the calibration curve f ($\bullet$) is a characteristic function for converting the variation attributable to absorption H ($\lambda$) to the hematocrit level Hct. The calibration curve f ($\bullet$) and a calibration curve g ($\bullet$) to be described later have been stored in the memory 62 in the form of a table as the calibration data 90 (see FIG. 5).

An absorbance value after reducing or eliminating the effects of light scattering and absorption (hereinafter called "corrected absorbance Dc") is provided by the following expression (19), using the expressions (12), (16), and (18):

$$Dc = (A(\lambda 2b) - p \cdot \lambda 2b - q)/(1 - Hct/100) \tag{19}$$

Finally, the concentration of the analyte (hereinafter called "quantified concentration Dm") is calculated using the calibration curve g ($\bullet$) at the wavelength $\lambda 2b$ by the following expression (20):

$$Dm = g(Dc) \tag{20}$$

Here, the calibration curve g ($\bullet$) is a characteristic function for converting the corrected absorbance Dc to the quantified concentration Dm. Thus, the quantified concentration Dm is obtained (step S5).

Hence, the absorbance correction section 84 corrects an absorbance measured at an arbitrary wavelength by using the variation attributable to absorption H ($\lambda$) so as to reduce or eliminate also the effects of absorption. Because the effects of absorption as well as scattering are dealt with, the analyte is measured with increased accuracy.

In step S6, information on the quantified concentration obtained in step S5 is shown on the display monitor 20. For this displaying process, the computing unit 60 first determines visible information to be shown on the display monitor 20, and then transmits a display control signal corresponding to the visible information to the display monitor 20. The visible information can include concentration and, by way of example, tendency, success/failure of measurement, time of measurement, and diagnosis.

The component measuring apparatus 10 has completed the blood-component measurement operation. A user can now detach the test tip 14 from the tip attachment part 16 and shut down the apparatus by pressing the power button 18.

Verification Experiments

Experiments were conducted to verify the benefits of the method for component measurement; the procedures and results of the experiments will now be described.
1. Sample Preparation First, whole blood was drawn from a specimen and centrifuged to separate plasma. Erioglaucine (available from Sigma-Aldrich Co, LLC.) was added to the plasma to produce solutions with different concentrations of dye component. Blood cell components were then added to the solutions to produce multiple samples with different dye concentrations and/or hematocrit levels. The design values for the dye concentrations were (1) 20 mg/dL, (2) 70 mg/dL, (3) 130 mg/dL, and (4) 220 mg/dL. Further, the design values for the hematocrit levels were (1) 25%, (2) 40%, and (3) 60%.
2. Calibration Curve for Hematocrit Level The multiple samples were aliquoted in hematocrit capillary tubes (VC-H075P, available from TERUMO CORPORATION) and centrifuged to provide individual observed values of hematocrit level Hct (%). The samples were also lysed and measured by a commercially available ultraviolet-visible spectrophotometer (V-530, available from JASCO Corporation) for their absorption spectra; absorbance at a wavelength ($\lambda 1$) of 540 nm was obtained for each sample. Each sample was then plotted with absorbance on the vertical axis versus hematocrit level on the horizontal axis.

Figure 10:
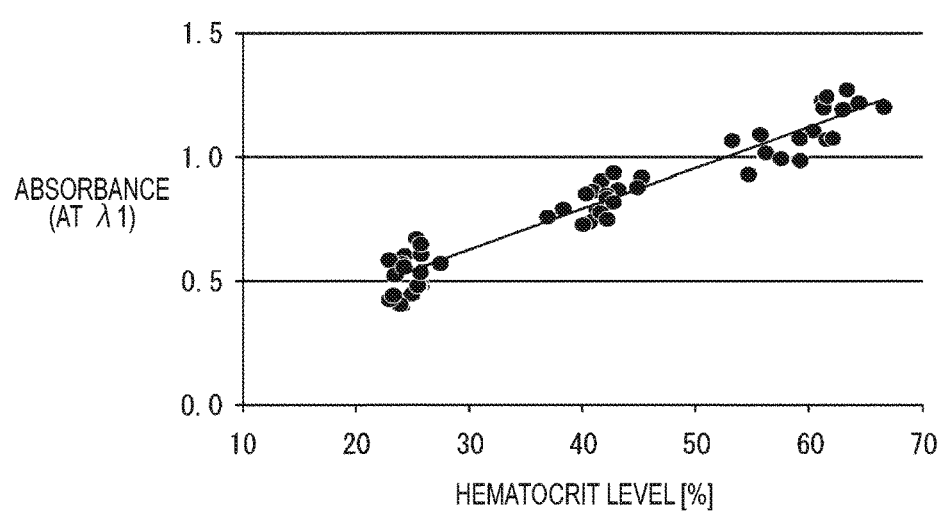
FIG. 10 is a graph presenting a calibration curve for hematocrit levels.

FIG. 10 is a graph presenting a calibration curve for hematocrit levels Hct. The solid line in the plot represents a regression line for a particular specimen or sample. As shown in the graph, there exists some data variation at different concentrations of erioglaucine, yet the variation is relatively normal taken as a whole, indicating that the calibration curve has a high linearity (positive correlation).
3. Verification a (Calibration Curve for Dye Concentration)

A first verification experiment determined a calibration curve for dye concentration at a wavelength $\lambda 2b$ of 630 nm. Specifically, each sample was plotted with absorbance corresponding to concentration on the vertical axis versus dye concentration on the horizontal axis. An observed absorbance A was used as a "comparative example," and a corrected absorbance Dc to be used as a "working example" was obtained by calculating a variation attributable to scattering S ($\lambda$) using a linear function.

Figure 11:
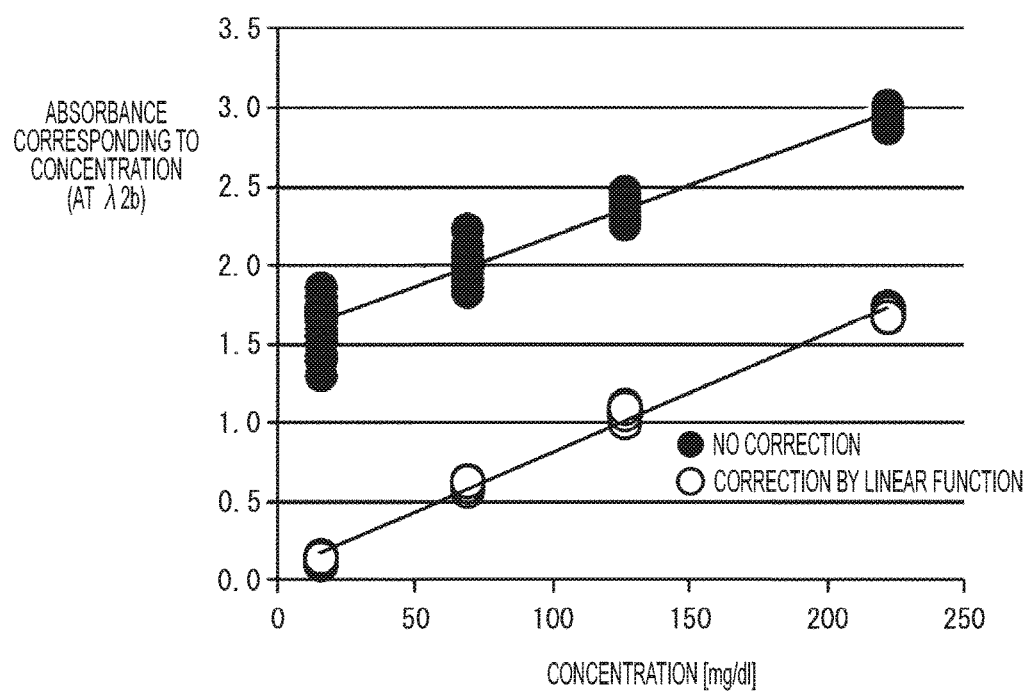
FIG. 11 is a graph presenting calibration curves for dye concentrations.

FIG. 11 is a graph presenting calibration curves for dye concentrations. The comparative example is plotted in black (hereinafter called "no correction") while the working example is plotted in white (hereinafter called "correction by linear function"). Further, the solid lines in the plot represent regression lines for particular specimens or samples.

As can be seen from the graph, the "no correction" shows data variation is large especially in the lower concentration regions, and also the linearity of the calibration curve is low. In contrast, the "correction by linear function" shows less data variation as a whole, with a higher linearity of the calibration curve.
4. Verification B (Quantification Accuracy)

A second verification experiment determined the accuracy in quantifying dye concentrations. Aside from the calibration curves shown in FIGS. 10 and 11, whole blood drawn from a specimen was used. The erioglaucine concentration was 220 mg/dL and the hematocrit level was 35% for the whole blood. The preceding procedures were taken to prepare multiple samples of the whole blood with the hematocrit levels of the samples being from 20% to 40%, and then the samples were measured according to the preceding procedures.

The characteristic curve as shown in FIG. 10 was used as the calibration curve f ($\bullet$) in the expression (18). Further, the characteristic curve as shown in FIG. 11 ("correction by linear function") was used as the calibration curve g ($\bullet$) in the expression (20).

Figure 12:
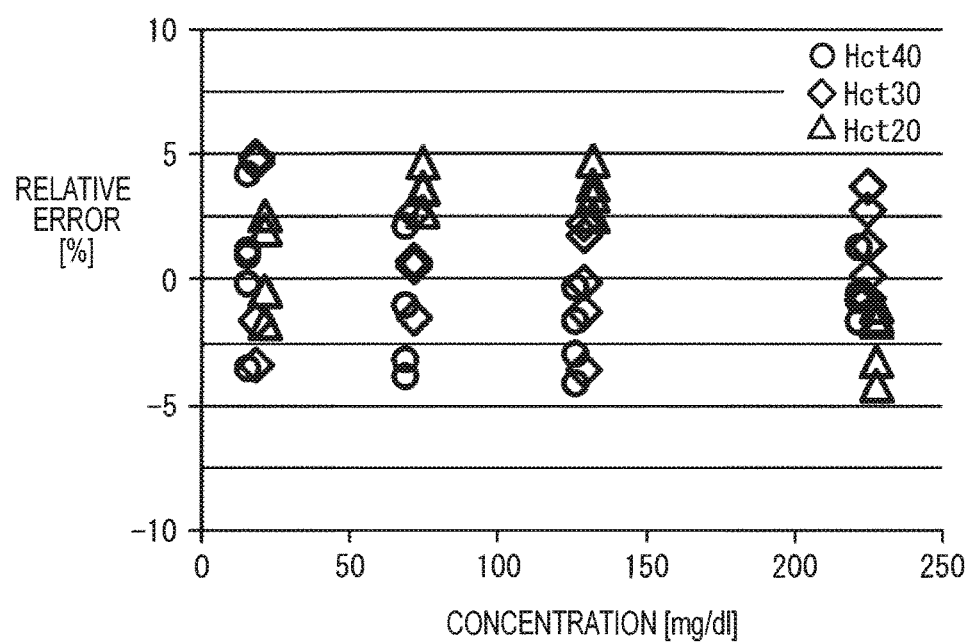
FIG. 12 is a graph presenting quantification errors by an embodiment of the method for component measurement.

FIG. 12 is a graph presenting quantification errors by the present method for component measurement. In the graph, relative error (unit: %) is on the vertical axis versus concentration (unit: mg/dL) on the horizontal axis. The "relative error" is calculated by the expression, 100×[(actual concentration)−(quantified concentration)]/(actual concentration). As can be seen from the graph, the relative errors are all within 5%, indicating that the method provides high quantification accuracy.

Application Examples

The dye component is not limited to erioglaucine as has been referred to in the above description, but other dye components that produce color reaction proportional to blood glucose level may also be used. Plasma glucose levels in whole blood can be measured by using those dye components. For example, the color reagent 42 can contain a combination of glucose oxidase (GOD), peroxidase (POD), 4-aminoantipyrine (4-AA), and N-ethyl-N-(2-hydroxy-3-sulfopropyl)-3,5-dimethylaniline (MAOS).

With the above content, plasma glucose in whole blood is catalyzed by GOD to form hydrogen peroxide proportional to the glucose concentration. In proportion to the amount of the produced hydrogen peroxide, 4-AA and MAOS condensate in the presence of POD to form a dye with the maximum absorbance at a wavelength $\lambda$ of 630 nm. Measuring the absorbance of the condensate enables measurement and quantification of glucose levels.

Benefits

As described above, the component measuring apparatus 10 is an apparatus for measuring an analyte, for example, a plasma component in a bodily fluid, based on the optical characteristics of a dye component, for example, erioglaucine, included in the bodily fluid after color reaction.

The component measuring apparatus 10 has: the data acquisition section 78 for acquiring the first observed value representing the absorbance (A) at the specific wavelength ($\lambda 1$) in the first wavelength region R1 in which a component (e.g., hemoglobin) other than the dye component has a relatively high light absorptivity and the group of second observed values representing the absorbances (A's) at one or more wavelengths ($\lambda 2a$ to $\lambda 2c$) in the second wavelength region R2 in which the light absorptivity is relatively low; the functional-form determination section 80 for determining a functional form that describes the wavelength characteristics of the variation attributable to scattering (S) and that is specified by one or more coefficients (p, q); the coefficient calculation section 82 for calculating the unknowns, the one or more coefficients (p, q), based on the first relational expression that involves the variation attributable to absorption (H) and the group of second relational expressions that do not involve the variation attributable to absorption (H); and the absorbance correction section 84 for correcting an absorbance measured at an arbitrary wavelength by using a function where the one or more coefficients (p, q) are applied to the functional form so as to reduce or eliminate at least the effects of scattering of light.

This configuration allows the number of degrees of freedom for the variation attributable to absorption (H) to be minimum (i.e., one), which in turn means that a small number of data values suffices for approximating to the wavelength characteristics of the variation attributable to scattering (S) with improved accuracy. Thus, the effects of light scattering can be appropriately reduced or eliminated even though the number of data values is small (for example, four), whereby sufficient accuracy in analyte measurement can be provided.

Addendum

The embodiments are not limited to those embodiments described above but can be freely varied without departing from the contemplated scope.

Samples are not limited to blood as was illustrated in the above embodiments. For example, a sample may be a bodily fluid containing lymph fluid, spinal fluid, or saliva. Further, any component in different kinds of bodily fluid is measurable in terms of its amount and/or properties.

The dye component in the above embodiments is formed by an addition of the color reagent 42 by way of example, however, a dye component in bodily fluid without an addition of the color reagent 42 (i.e., a raw bodily fluid) may also be measured.

The light emitter 66 in the above embodiments includes different kinds of light sources 67, 68a, 68b, and 68c by way of example, however, it may be configured by combining a single light source with different kinds of optical filters (of a band-pass type) disposed in front of the light source.

The invention claimed is:

1. A component measuring apparatus for measuring an analyte in a bodily fluid based on optical characteristics of a dye component contained in the bodily fluid before or after color reaction, comprising:
   an optical measurement system comprising a light emitter and a light receiver;
   a processor; and
   a memory coupled with and readable by the processor and storing therein instructions that, when executed by the processor, cause the processor to:
      instruct the optical measurement system to direct light, via the light emitter, toward a test tip comprising the bodily fluid;
      receive a signal corresponding to an amount of the light reflected from the test tip, wherein the signal is provided by the light receiver;
      acquire, based on the received signal, a first observed value representing an absorbance at a specific wavelength in a first wavelength region in which a component of the bodily fluid other than the dye component has a first amount of light absorptivity and a group of second observed values representing absorbances at one or more different wavelengths in a second wavelength region in which the component of the bodily fluid other than the dye component has a second amount of light absorptivity, wherein the first amount of light absorptivity is higher than the second amount of light absorptivity, and wherein the dye component has a third amount of light absorptivity in the second wavelength region higher than the second amount of light absorptivity;
      determine a functional form which describes wavelength characteristics of a variation attributable to scattering that indicates an absorbance variation attributable to scattering of light in the bodily fluid, and is defined by one or more coefficients;
      determine the one or more coefficients based on a first relational expression for the first observed value, involving a variation attributable to absorption that indicates an absorbance variation attributable to absorption of light in the bodily fluid, and a group of second relational expressions for the second observed values, not involving the variation attributable to absorption;
      correct an absorbance measured at an arbitrary wavelength using a function where the determined one or more coefficients are applied to the determined functional form so as to reduce or eliminate at least the effects of the light scattering; and
      determine, based on the corrected absorbance measured, an amount of concentration of the dye component in the bodily fluid.

2. The component measuring apparatus according to claim 1, wherein correcting the absorbance measured at the arbitrary wavelength includes using the variation attributable to absorption so as to further reduce or eliminate the effects of the light absorption.

3. The component measuring apparatus according to claim 1, wherein determining the one or more coefficients based on the first relational expression expressing that a sum of an absorbance corresponding to concentration of the dye component, the variation attributable to scattering, and the variation attributable to absorption equals the first observed value, and the group of second relational expressions expressing that a sum of the absorbance corresponding to concentration and the variation attributable to scattering equals the second observed values.

4. The component measuring apparatus according to claim 3, wherein a constraint is added in determining the one or more coefficients, the constraint being an absorption spectral similarity regardless of concentrations of the dye component.

5. The component measuring apparatus according to claim 4, wherein determining the functional form is based on a number of the one or more coefficients, the number being smaller than a number of the second observed values.

6. The component measuring apparatus according to claim 1, wherein the functional form is any one of a polynomial function, a power function, and an exponential function.

7. The component measuring apparatus according to claim 1, wherein the first observed value and the group of second observed values are acquired in wavelength intervals of at least 20 nm.

8. The component measuring apparatus according to claim 1, wherein the bodily fluid is blood comprising hemoglobin, and the first observed value is acquired in the first wavelength region at 400 nm to 600 nm and the group of second observed values is acquired in the second wavelength region at 600 nm to 1000 nm.

9. The component measuring apparatus according to claim 1, wherein the bodily fluid is blood, and the dye component is a component that develops color proportional to a glucose level in the blood.

10. A method for component measurement for measuring an analyte in a bodily fluid based on optical characteristics of a dye component contained in the bodily fluid before or after color reaction, comprising:
    instructing, by a processor, an optical measurement system to direct light, via a light emitter, toward a test tip comprising the bodily fluid;
    receiving, by the processor and via a light receiver of the optical measurement system, a signal corresponding to an amount of the light reflected from the test tip;
    acquiring, by the processor and based on the received signal, a first observed value representing an absorbance at a specific wavelength in a first wavelength region in which a component of the bodily fluid other than the dye component has a first amount of light absorptivity;
    acquiring, by the processor and based on the received signal, a group of second observed values representing absorbances at one or more different wavelengths in a second wavelength region in which the component of the bodily fluid other than the dye component has a second amount of light absorptivity, wherein the first amount of light absorptivity is higher than the second amount of light absorptivity, and wherein the dye component has a third amount of light absorptivity in the second wavelength region higher than the second amount of light absorptivity;
    determining, by the processor, a functional form which describes wavelength characteristics of a variation attributable to scattering that indicates an absorbance variation attributable to scattering of light in the bodily fluid, and is defined by one or more coefficients;
    determining, by the processor, the one or more coefficients based on a first relational expression for the first observed value, involving a variation attributable to absorption that indicates an absorbance variation attributable to absorption of light in the bodily fluid, and a group of second relational expressions for the second observed values, not involving the variation attributable to absorption;
    correcting, by the processor, an absorbance measured at an arbitrary wavelength using a function where the determined one or more coefficients are applied to the determined functional form so as to reduce or eliminate at least the effects of the light scattering; and
    determining, by the processor and based on the corrected absorbance measured, an amount of concentration of the dye component in the bodily fluid.

11. A program stored a non-transitory medium, the program comprising instructions for measuring an analyte in a bodily fluid based on optical characteristics of a dye component contained in the bodily fluid before or after color reaction, the instructions comprising:
    instructions to instruct an optical measurement system to direct light, via a light emitter, toward a test tip comprising the bodily fluid;
    instructions to receive, via a light receiver of the optical measurement system, a signal corresponding to an amount of the light reflected from the test tip;
    instructions to acquire, based on the received signal, a first observed value representing an absorbance at a specific wavelength in a first wavelength region in which a component of the bodily fluid other than the dye component has a first amount of light absorptivity;
    instructions to acquire, based on the received signal, a group of second observed values representing absorbances at one or more different wavelengths in a second wavelength region in which the component of the bodily fluid other than the dye component has a second amount of light absorptivity, wherein the first amount of light absorptivity is higher than the second amount of light absorptivity, and wherein the dye component has a third amount of light absorptivity in the second wavelength region higher than the second amount of light absorptivity;
    instructions to determine a functional form which describes wavelength characteristics of a variation attributable to scattering that indicates an absorbance variation attributable to scattering of light in the bodily fluid, and is defined by one or more coefficients;
    instructions to determine the one or more coefficients based on a first relational expression for the first observed value, involving a variation attributable to absorption that indicates an absorbance variation attributable to absorption of light in the bodily fluid, and a group of second relational expressions for the second observed values, not involving the variation attributable to absorption;
    instructions to correct an absorbance measured at an arbitrary wavelength using a function where the determined one or more coefficients are applied to the determined functional form so as to reduce or eliminate at least the effects of the light scattering; and
    instructions to determine, based on the corrected absorbance measured, an amount of concentration of the dye component in the bodily fluid.

12. The method according to claim 10, further comprising correcting by the processor, the absorbance measured at an arbitrary wavelength using the variation attributable to absorption so as to further reduce or eliminate the effects of the light absorption.

13. The method according to claim 10, further comprising determining, by the processor, the one or more coefficients based on the first relational expression expressing that the sum of an absorbance corresponding to concentration of the dye component, the variation attributable to scattering, and the variation attributable to absorption equals the first observed value, and the group of second relational expressions expressing that the sum of the absorbance corresponding to concentration and the variation attributable to scattering equals the second observed values.

14. The method according to claim 13, further comprising adding, by the processor, a constraint in calculating determining the one or more coefficients, the constraint being an absorption spectral similarity regardless of concentrations of the dye component.

15. The method according to claim 14, further comprising determining the functional form based on a number of the one or more coefficients, the number being smaller than a number of the second observed values.

16. The method according to claim 10, further comprising determining the functional form that is any one of a polynomial function, a power function, and an exponential function.

17. The method according to claim 10, further comprising acquiring the first observed value and the group of second observed values with wavelength intervals of at least 20 nm.

18. The method according to claim 10, wherein the bodily fluid is blood comprising hemoglobin, and further comprising acquiring, by the processor, the first observed value in the first wavelength region at 400 nm to 600 nm and the group of second observed values in the second wavelength region at 600 nm to 1000 nm.

19. The method according to claim 10, wherein the bodily fluid is blood, and the dye component is a component that develops color proportional to a glucose level in the blood.

20. The method according to claim 10, wherein a boundary between the first wavelength region and the second wavelength region is based on an absorption quality of the bodily fluid.

* * * * *